United States Patent
Pätilä et al.

(10) Patent No.: US 12,161,719 B2
(45) Date of Patent: Dec. 10, 2024

(54) METHOD OF ENHANCING THE ANTIMICROBIAL ACTION OF SYSTEMICALLY ADMINISTERED ANTIBIOTICS

(71) Applicant: Koite Health Oy, Espoo (FI)

(72) Inventors: Tommi Pätilä, Espoo (FI); Sakari Nikinmaa, Espoo (FI); Juha Rantala, Espoo (FI)

(73) Assignee: Koite Health Oy, Espoo (FI)

( * ) Notice: Subject to any disclaimer, the term of this patent is extended or adjusted under 35 U.S.C. 154(b) by 380 days.

(21) Appl. No.: 16/983,171

(22) Filed: Aug. 3, 2020

(65) Prior Publication Data

US 2021/0030874 A1    Feb. 4, 2021

(30) Foreign Application Priority Data

Aug. 2, 2019 (FI) ..................................... 20195661

(51) Int. Cl.
*A61K 41/00* (2020.01)
*A61K 9/00* (2006.01)
*A61K 31/65* (2006.01)
*A61K 31/7052* (2006.01)
*A61K 49/00* (2006.01)
*A61P 31/04* (2006.01)

(52) U.S. Cl.
CPC .......... *A61K 41/0057* (2013.01); *A61K 9/006* (2013.01); *A61K 31/65* (2013.01); *A61K 31/7052* (2013.01); *A61K 49/0034* (2013.01); *A61P 31/04* (2018.01)

(58) Field of Classification Search
CPC .... A61K 41/0057; A61K 9/006; A61K 31/65; A61K 31/7052; A61K 49/0034; A61K 45/06; A61P 31/04; A61P 1/02; A61P 11/00; A61P 27/16; A61P 31/12; A61N 5/062; A61N 5/0624
See application file for complete search history.

(56) References Cited

U.S. PATENT DOCUMENTS

| | | |
|---|---|---|
| 2002/0165594 A1 | 11/2002 | Biel |
| 2004/0122491 A1 | 6/2004 | Strong |
| 2004/0193235 A1 | 9/2004 | Altshuler et al. |
| 2005/0059731 A1 | 3/2005 | Albrecht et al. |
| 2011/0218139 A1 | 9/2011 | Robinson et al. |
| 2016/0304453 A1 | 10/2016 | Rogelj et al. |
| 2019/0160129 A1 | 5/2019 | McFarland |
| 2021/0387013 A1* | 12/2021 | Nikinmaa .......... A61K 41/0057 |

FOREIGN PATENT DOCUMENTS

| | | | | |
|---|---|---|---|---|
| CN | 102652028 | A | | 8/2012 |
| CN | 108697750 | A | | 10/2018 |
| CN | 109091685 | A | | 12/2018 |
| GB | 2454652 | A | * 5/2009 | ............. A61N 5/062 |
| JP | 2018535250 | A | | 11/2018 |
| WO | WO0152814 | A1 | | 7/2001 |
| WO | WO2005034855 | A2 | | 4/2005 |
| WO | WO2005074987 | A1 | | 8/2005 |
| WO | WO2009014524 | A2 | | 1/2009 |
| WO | WO2017059255 | A1 | | 4/2017 |

OTHER PUBLICATIONS

Biel et al., Int. Forum Allergy Rhinol. 2011; 1(5): 329-334. (Year: 2011).*
Parasher et al., Am. J. Otolaryngol. 40 (2019) 467-472. (Year: 2019).*
Blanco et al. Photodiagnosis and Photodynamic Therapy 18 (2017) 138-139. (Year: 2017).*
Setiawatie et al: Comparision of anti bacterial efficacy of photodynamic therapy and doxycycline on aggregatibacter actinomycetemcomitans. J. Infect. Dis., Mar. 7, 2018, vol. 12 (S), pp. 95-103.
Tavares: Antimicrobial photodynamic therapy alone or in combination with antibiotic local administration against biofilms of Fusobacterium nucleatum and Porphyromonas gingivalis. Journal of Photochemistry & Photobiology, B: Biology, Sep. 12, 2018, pp. 135-145.
Zhang et al: Modern Practical Stomatology. Jilin Science and Technology Press, vol. 1, 2016, pp. 211-212.
Looking Fit: Sunlight and the skin. Feb. 2005. pp. 86, 88, 90.
Setiawatie et al: Comparison of antibacterial efficacy of photodynamic therapy and doxycycline on aggregatibacter actinomycetemcomitans. Afr., J. Infect. Dis., Mar. 7, 2018, vol. 12(S), pp. 95-103.

* cited by examiner

*Primary Examiner* — Robert S Cabral
(74) *Attorney, Agent, or Firm* — Laine IP Oy; Mark W. Scott (57) ABSTRACT

Antibiotic for use in a method comprising systemically administering a photosensitive antibiotic to a subject having a microbial infection in a target tissue to provide a blood plasma concentration of the antibiotic in the subject; allowing the plasma or tissue concentration of the antibiotic increase to a predetermined level; and subjecting the target tissue to photodynamic therapy in order to increase the antimicrobial action of the antibiotic in the target tissue. With light activation the efficacy of the photosensitizer antibiotic can be enhanced, the spectrum of the microbial effect broadened and even an antiviral effect can be obtained. Generally, the present invention can be exploited when there is a need for enhancement of the local antimicrobial effect of antibiotics.

33 Claims, 3 Drawing Sheets

METHOD OF ENHANCING THE ANTIMICROBIAL ACTION OF SYSTEMICALLY ADMINISTERED ANTIBIOTICS

FIELD OF INVENTION

The present invention relates to methods of enhancing the antimicrobial and therapeutic action of systemically administered antibiotics, in particular photosensitive antibiotics. The present invention also relates to systemically administered antibiotic for use in antimicrobial therapies, kits for enhancing the antimicrobial and therapeutic action of systemically administered antibiotics, as well as methods of enhancing the enzyme inhibition action of a pharmaceutical substance having an antimicrobial activity.

BACKGROUND

Periodontal diseases, similar to tooth decay, are typically related to microbial infections. Dysbiotic dental plaque accumulate at the gums and eventually the overriding immune system in concert to the infection leads to destruction of the periodontal tissues. Because the bacteria live within biofilms in dental plaque, most traditional antibacterial treatments with antibiotics have little or none effect in chronic dental or periodontal treatment.

When administered even at low doses tetracyclines have, however, been shown to be effective in treatment of periodontal diseases. Thus, doxycycline and minocyline, broad-spectrum antibiotics, of the tetracycline class are a common treatment protocol for periodontitis in different concentrations ranging from ultra-low to ultra-high concentrations. Two major doxycycline products, viz. Periostat® and Atridox®, have been introduced on the market using doxycycline for treatment of periodontal diseases.

Formulated for oral administration, Periostat® uses low dose doxycycline, whereas Atridox® is formulated as a gel for sub-gingival administration. On the other hand, Arestin® is a locally administered minocycline microsphere gel with slow drug release. Similarly azithromycin, a macrolide antibiotic has shown to have an effect on the periodontitis, but also to the drug induced gingival overgrowth.

The proven efficacy of the tetracycline or macrolide groups of drugs in the management of periodontal diseases may be related not only to their antibacterial actions, but to a number of additional properties that have been recently identified. These include wide range of collagenase inhibition, including direct inhibition of a range of matrix metalloproteinase (MMP) enzymes, but also their gene expression. In addition, they suppressed transcription factors, downregulation of which leading to inhibition of pro-inflammatory cytokines and MMP activity. They inhibit bone resorption, and are able to promote the attachment of fibroblasts to root surfaces.

Tetracyclines carry bacteriostatic action and inhibit the growth and multiplication of bacteria. They enter the bacteria in two distinct mechanisms, passive diffusion and energy dependent active transport system. By binding to 30S subunit of the ribosome and blocking the attachment of transfer RNA, they inhibit protein synthesis. Like all macrolide antibiotics, azithromycin reversibly inhibits bacterial protein synthesis by targeting the 23S ribosomal RNA of the 50S ribosomal subunit in susceptible organisms.

The present-day antibiotic treatments of periodontal diseases are unsatisfactory in several respects. It has been found that when the exposure to tetracycline is removed, the bacteria continue to grow. On the other hand, extensive use of bactericidal agents is undesired due to the triggering of antibacterial resistance formation and side effects related to gut microbiome changes.

Systemically administered antibiotics have side effects such as vomiting, diarrhea, rash, loss of appetite and potentially kidney problems, which also hamper their use for treatment of localized microbial infections. Local administration of antibiotics will achieve higher concentrations directly at infected sites and reduce possible systemic side effects.

However, local administration requires proper detection of the infected site or sites and correct topical application, which may need to be renewed several times depending on the condition and accessibility of the infected tissue.

SUMMARY OF THE INVENTION

It is an aim of the present invention to eliminate at least a part of the problems relating to the art.

In a first object, the present invention provides a method of enhancing the antimicrobial action of a systemically administered antibiotic.

In a second object, the present invention provides a systemically administered antibiotic for use in antimicrobial therapy of local microbial infections.

In a third object, the present invention provides a method of enhancing matrix enzyme inhibition action of a pharmaceutical substance having antimicrobial activity.

In a fourth object, the present invention provides a kit for enhancing the antimicrobial action of a systemically administered antibiotic.

In a fifth object, the present invention provides a method of enhancing the enzyme inhibition action of a cyclic antibiotic for inhibition of collagenase enzyme activity.

In the present invention it has been found that systemic administration of antibiotics can be combined with local application of photodynamic therapy to achieve an enhanced local antimicrobial action, in particular antibacterial action, of the systemically administered antibiotic.

Thus, provided are systemically administered antibiotics for use in antimicrobial photodynamic therapy of local, in particular topical, microbial infections.

A method of enhancing the antimicrobial action of an antibiotic, comprises the steps of:
  systemically administering a photosensitive antibiotic to a subject having a microbial infection in a target tissue to provide a blood plasma concentration of said antibiotic in said subject; and
  subjecting the target tissue to photodynamic therapy in order to enhance (i.e. to increase) the action, in particular antimicrobial action, of the antibiotic in the target area or tissue.

The method can also be used for enhancing the enzyme inhibition action of a pharmaceutical substance having an antimicrobial activity as well as for enhancing the enzyme inhibition action of a cyclic photoactive antibiotic for inhibition of collagenase enzyme activity, More specifically, the present invention is mainly characterized by what is stated in the characterizing parts of the independent claims.

Considerable advantages are obtained by the present invention. Thus, it has been observed that with light activation the efficacy of the photosensitizer antibiotic can be enhanced by up to 50% or even more. It would appear, although this is merely one possible explanation, that the production of reactive oxygen by the antibiotic molecule changes partly the mechanism of action. As a result, locally (i.e. topically) administered light enhances the bactericidity of the molecule.

Due to the antimicrobial photodynamic effect, the spectrum of the microbial effect can also be broadened. Also, an antiviral effect can be obtained. Thus, generally, the present invention can be exploited when there is a need for enhancement of the local antimicrobial effect.

Potentiating antibiotic activity with light or with combination of tissue healing and bacteria killing light has immense potential in promoting periodontal healing and in general oral bacteria management. It has been shown in studies of children with hearth problems that antibiotic treatment can reduce the formation of caries. In the present context it has been shown that the antibiotic effect of certain antibiotics can be increased with light activation.

Periodontal diseases are often difficult to treat, and presently constant low dose and ultra-low dose use of doxycycline has been proposed for treatment of periodontitis and treat and prevent peri-implant mucositis. Use of light activation to promote gum tissue healing and to increase the antibacterial effect of antibiotic treatment is new novel approach to treat gum health.

Further details and advantages of various embodiments will appear from the following detailed description of embodiments.

DESCRIPTION OF EMBODIMENTS

In the present context, "photodynamic therapy", also referred to by the abbreviation "PDT", stands for any therapy where light is converted to some form of reactive oxygen.

In the present context, the concept of "photodynamic therapy" also includes therapies wherein heat is generated in addition to reactive oxygen, which may be referred to as "photothermal therapy". Thus, in some embodiments, as much as up to about 90 to 92% of the energy input (electric energy) is converted into thermal energy whereas 8 to 10% of the energy is converted into reactive oxygen.

Examples of "reactive oxygen" include singlet oxygen, oxygen radicals and oxygen ions.

"Exogenous" when used in relation to bacteria stands for "outside" of the bacteria "Endogenous" stands for "inherently present" in the bacteria. When used with reference to molecules and substances in the bacteria, "endogenous" is used interchangeably with the term "intracellular".

In the present context, "mammals" have the conventional meaning in the art. Particularly interesting targets are humans and animals kept for husbandry and as pets, including dogs, cats, rabbits, horses, cattle, sheep, goats and pigs.

"Non-coherent" when used in connection to light means that the amplitude and phase of the emitted light waves fluctuate randomly in space and time. One embodiment comprises using LEDs as non-coherent light sources. Another embodiment comprises using UVC lamps as non-coherent light sources.

"Antimicrobial photodynamic therapy", also referred to by the abbreviation "aPDT", is a photochemistry-based method that uses photons to activate "sensitizers" that, in the activated state, impart antimicrobial effect. Thus, in one embodiment, aPDT is carried out in conjunction with photosensitizers.

"Antimicrobial blue light", also referred to by the abbreviation "aBL", is light, typically in the wavelength area of 405 to 470 nm, that exhibits intrinsic antimicrobial effect without the involvement of exogenous photosensitizers.

"High energy photons" are photons with energy in the range from 3.5 eV to 2.8 eV, in particular about 3.2 to 2.9 eV or 3.17 to 2.95 eV. Typically, such photons are contained in light having a wavelength in the range of about 350-450 nm, for example about 370 to 410 nm.

"Low energy photons" are photons with energy in the range from 1.24 eV to 2.48 eV, in particular 1.3 to 2.4 eV, for example 1.4 to 1.6 eV or 1.45 to 1.56 eV. Typically, such photons are contained in light having a wavelength in the range of about 500 to 1000 nm, for example about 780 to 830 nm.

Light with photons having "a majority energy in the range from 3.5 eV to 2.8 eV" stands for light, for example in the form of a light beam or light ray, in which at least 50%, in particular at least 60% or at least 70% or at least 80% or at least 90% or at least 95%, of the photons—as indicated by their energy—have an energy in the range from 3.5 eV to 2.8 eV.

Light with photons having "a majority energy in the range from 1.24 eV to 2.48 eV" stands for light, for example in the form of a light beam or light ray, in which at least 50%, in particular at least 60% or at least 70% or at least 80% or at least 90% or at least 95%, of the photons—as indicated by their energy (or wavelength)—have an energy in the range from 1.24 eV to 2.48 eV.

In the present context, a specific value of a wavelength will typically include a range about that specific value, for example of 5 to 35 nm, such as 5 to 20 nm, in particular about 10 to 15 nm, on either side of the value. Thus, for example, "405 nm" will be considered to include a range of wave lengths of about 395 nm to 415 nm, i.e. 405 nm±10 nm. Similarly, "810 nm" will be considered to include a range of wavelengths of about 395 nm to 825 nm, i.e. 810 nm±15 nm.

In one embodiment, light, in particular non-coherent light, is provided by an optoelectronic device comprising light-emitting diode(s) (i.e. LEDs) as a light source.

"Photosensitizers" are compounds or molecules that are capable of absorbing electromagnetic radiation for example in the ultraviolet or visible region and transferring it to adjacent molecules. Typically, the photosensitizers have de-localized π systems.

The photosensitizers can be naturally occurring compounds ("natural photosensitizers") and synthetic compounds.

"Antibacterial photodynamic therapy" stands for a method, where light activated photosensitizer produces reactive oxygen species, out of which the singlet oxygen is the most important. The exposure to the singlet oxygen causes disruption of cellular structures including lipid membranes. The effect is most prominent in gram positive bacteria, where the lack of excess reactive oxygen cleansing means are compromised. This is the case for example in streptococci species lacking the catalase enzyme, such as *Streptococcus mutans*. Examples of other gram-positive bacteria which can be subjected to the present treatment include bacteria of the genera *Staphylococcus*, such as *Staphylococcus aureaus, Corynebacterium, Clostridium, Mycobacterium, Nocardia, Listeria, Bacillus*.

"Photosensitive" when used in conjunction with antibiotics denotes the ability of the antibiotic molecule to absorb light of specific wavelength and emit the light forward to activate a nearby oxygen molecules, providing reactive oxygen species (ROS).

"Systemic antibiotics" are antibiotics which usually are given orally or parenterally (or possibly transdermally) and which generally affect the whole body. Thus, a systemic antibiotic will typically have an antimicrobial effect that occurs in tissues distant from the site of contact between the body and antibiotic. Systemic antibiotics will after administration give rise to a concentration of the antibiotics in the plasma of the subject to which it has been give.

Several antibiotic molecules, such as tetracyclines and macrolides, act as photosensitizers, in addition to their basic antibiotic function. The photosensitizing action has been acknowledged as photosensitivity during antibiotic treatment. For example, the photosensitivity of doxycyline and azithromycine must be taken into account during the treatment period, due to which the patients are advised to avoid direct sunlight.

The reactive oxygen species released during photosensitizing of the antibiotic are toxic to several kinds of microbes, including bacteria, viruses, fungi and parasites. Of the reactive oxygen species released during photosensitizing of the antibiotic, singlet oxygen is the most potent of the ROS species, due to the relatively long half-life amounting to microseconds. This mechanism is known as antimicrobial photodynamic therapy (aPDT). Antibiotic molecules absorb low wavelength light and these wavelengths are usually well absorbed in skin tissue, thus the photosensitivity is generally well tolerated.

One embodiment comprises a method of enhancing the antimicrobial action of an antibiotic. In the method a systemically acting, photosensitive antibiotic is administered to a subject having a microbial infection in a target tissue to provide a blood plasma concentration of said antibiotic in said subject;
optionally allowing the plasma concentration of the antibiotic increase to a predetermined level; and
subjecting the target tissue to photodynamic therapy in order to increase the antibiotic action of the antibiotic in the target tissue.

The term "subject" covers generally any animals, which have a circulatory system. In particular, "subject" refers to mammals, such as humans.

Administration of the systemic antibiotic can take place primarily orally or parenterally but also transdermally or generally in any way which will lead to an increase in the concentration of the antibiotic in the blood plasma. The selection of administration route will typically depend on whether the antibiotics are absorbed in the intestine or not.

In one embodiment, the tissue concentration of the antibiotic is increased by oral mucosal delivery.

One embodiment comprises allowing the plasma concentration to increase to at least 10%, in particular 20 to 100%, of the administered antibiotics' maximum plasma concentration (i.e. peak plasma concentration, $C_{max}$, of the antibiotic after administration).before subjecting the target tissue to photodynamic therapy The "target tissue" means tissue which will be subjected to photodynamic therapy. Typically, the target tissue is tissue which exhibits antimicrobial infection. In one embodiment, the target tissue includes the following: soft tissues, biofilms, saliva, skin, plaque and teeth surfaces and mucous membranes of a subject (as defined in the foregoing).

In one embodiment, the target tissue tissues comprise oral tissue, such as tissue in the oral cavity, including gum and oral mucosa as well as underlying tissue.

In one embodiment, the target tissue comprises tissue in the throat, in the nose or in the ears.

In one embodiment, the target tissue exhibits a microbial infection. In particular, the target tissue comprises a gumline bacterial biofilm, or the target tissue exhibits pharyngitis or otitis.

In one embodiment, the target tissue exhibits a thin layer of tissue which is translucent to light or which can be traversed by light of the above-mentioned wavelengths. An example of such tissue is the ear drum. Other examples include tissues in the respiratory system and the respiratory tract.

In one embodiment, the antibiotic concentration is increased in the Gingival Precrevicular Fluid.

The present embodiments can be carried out for microbial infections caused by viruses, bacteria or fungi.

In one embodiment, the microbial infection to be treated is caused by gram-negative bacteria, in particular selected from the group of *Proteobacteria, Aquificae, Chlamydiae, Bacteroidetes, Chlorobi, Cyanobacteria, Fibrobacteres, Verrucomicrobia, Planctomycetes, Spirochetes, Acidobacteria, Actinobacteria* (such as *Aggregatibacter actinomycetemcomitans*) *Firmicutes, Thermotogae, Porphyromonas* (such as *Porphyromonas gingivalis*) and *Chloroflexi*.

In one embodiment, the microbial infection to be treated is caused by virus selected from the group of Adenoviruses, Herpesviruses, Poxviruses, Parvoviruses, Reoviruses, Picornaviruses, Togaviruses, Orthomyxoviruses, Rhabdoviruses, Retroviruses, Papillomavirus and Hepadnaviruses In one embodiment, the systemically active antibiotic is selected from the group of ciprofloxacin, doxycycline, levofloxacin, ofloxacin, tetracycline, trimethoprim, azithromycin, and macrolide. Tetracycline type antibiotics are particularly interesting. In one embodiment, the antibiotics are selected from the group of clarithromycin, erythromycin, roxithromycin, or azithromycin; tetracyclines including doxycycline, ionocycline, tetracycline, chlortetracycline, demeclocycline, lymecycline, meclocycline, methacycline, rolitetracycline, tigecycline, eravacycline, sarecycline, omacycline, sarecycline, eravacycline, omadacycline, oxytetracycline; other antibiotics such as colchicine, trimethoprim or metronidatzole. In particular the antibiotics are selected from azithromycin, doxycycline, minocycline or colchicine or metronidatzole, or any of their combinations.

Once the blood plasma concentration of the antibiotic has reached a predetermined level, the target tissue is subjected to photodynamic therapy in order to topically increase the antibiotic action of the systemic antibiotic. In particular, the antibiotic is photoactivated in order to eliminate pathogens inside tissue and host cells.

The antibiotic can be administered at conventional dosages, typically ranging from 0.1 to 50 mg/kg body weight, for example 0.5 to 5 mg/kg body weight as a daily dosage, depending on the antibiotic. The actual dosage will depend on the pharmaceutical preparation, whether the antibiotic is formulated for immediate release or extended-release.

For example, doxycycline can be administered at the usual dose of 1 to 2 mg/kg body weight, for instance following a dosage regime of 200 mg on the first day of treatment (for example at 100 mg every 12 hours) followed by a maintenance dose of 100 mg/day.

Azithromycin can be administered in the form of immediate-release preparations at 500 mg orally as a single dose on the first day of the treatment, followed by 250 mg orally once a day during the next 4 days. For extended-release typically 2 g orally once as a single dose for an adult is recommended. Parenterally, azithromycin can be administered as a 500 mg IV dose once a day as a single dose for at least 2 days, which can be combined with 500 mg of an oral, e.g. immediate-release formulation, during the remaining period of a 7-day to 10-day course of therapy.

Minocycline can be administered to adults perorally or intravenously at an initial dosage of 200 mg following by 100 mg every 12 hours. It can also be administered more frequently, for example 6 times a day, at a higher total dosage of up to 300 mg/day, Also for the other antibiotics listed above, conventional dosage regimes can be applied. However, when combined with photodynamic treatment as described herein, the individual or total dosages of the antibiotics can be reduced with at least 10%, and even up to 50%, while still achieving the intended effect in the tissue targeted by the photodynamic treatment.

In one embodiment, the systemic photosensitive antibiotic is combined with topically administered photosensitizer to enhance antimicrobial PDT treatment on tissue and inside tissue, in particular to enhance treatment effect against skin diseases affecting epidermis and dermis and to enhance the treatment penetration into gum tissue in treatment of gum disease.

In one embodiment, the photodynamic therapy comprises subjecting the target tissue to electromagnetic radiation in the form of light of either or two of the following energy levels: a first light with photons having a majority energy in the range from 3.5 eV to 2.8 eV and a second light with photons having a majority energy in the range from 1.24 eV to 2.48 eV, wherein photons of the first light and the second light are simultaneously directed against the target tissue.

In one particularly preferred embodiment,
non-coherent radiant light energy is generated at one first energy level, or preferably at, at least, two different energy levels, a first and a second energy level;
from the non-coherent radiant light energy there is provided first light having a wavelength corresponding to the majority energy of the first energy level, and optionally a second light having a wavelength corresponding to the majority energy of the second energy level; and
the first and optionally the second light are then simultaneously directed against the target tissue, in particular against the surface of the target tissue.

In one embodiment, the target tissue is subjected to endogenous and exogenous excitement, in particular so as to generate reactive oxygen singlets or reactive oxygen species or both.

In one embodiment, the target tissue is subjected to electromagnetic radiation at a dosage of 1 to 200 $J/cm^2$ and typically at a power density of 10 to 5000 $mW/cm^2$ for a period of time from 0.5 s to 120 min.

In one embodiment, light is used as such, i.e. without any photosensitizer.

In another embodiment, light is combined with at least one photosensitive substance for treating the surface using photodynamic therapy. Particularly, the photosensitive substances are selected from the group of Hypericin, curcumin, phenalenone derivatives, Cercosporin, psoralen, xanthotoxin, Angelicin, alpha-Terthienyl, Phenylthepatriyne, THC, Cannabidiol (CBD). Synthetic photosensitizers include the following: RB (Rose Bengal), MB, Porphyrin derivatives, Curcumin derivatives, Methylene Blue, Indocyanine Green, Erythosine, Phenalenone derivatives, Fullerene derivatives, Xanthene derivates and combinations thereof.

In one embodiment, high energy photons and low energy photons are applied in conjugation with at least one exogeneous photosensitizer, which can be activated with the low energy photons.

In one embodiment, a photosensitizer is provided for use in topical treatment of mammal tissues. The sensitizer is preferably applied to a superficial part of the tissue, such as on mammal skin or on a mucous membrane and the part thus treated is subsequently or simultaneously subjected to light at two different wavelengths.

Generally, the photosensitizer can be applied onto the target tissue typically from a liquid (solution or dispersion) or from a solid formulation or semisolid formulation, such as a gel, cream or ointment. The formulation may contain conventional excipients, solvents and fillers, in addition to the photosensitizer substance. Typically, the concentration of the photosensitizer in the formulation can vary within broad ranges from about 0.001 mg/g to 500 mg/g, for example about 0.01 mg/g to 200 mg/g.

Usually, the photosensitizer is allowed to sorb onto or into the tissue before initiation of the photodynamic therapy. The time allowed for the application and sorption of the photosensitizer can vary from about 1 s to 240 min, typically 10 s to 120 min, for example 15 s to 60 min.

In one embodiment, a combination of first light having a wavelength of 405 nm±10 nm and second light having a wavelength of 810 nm±15 nm is used, both the first and the second lights comprising non-coherent light, for example produced by optoelectronic devices, such as light emitting diodes (LEDs).

In one embodiment, a combination of first light having a wavelength of 405 nm±10 nm, second light having a wavelength of 810 nm±15 nm, and third light having a wavelength of 780 nm±10 nm is used, the first, the second and the third lights comprising non-coherent light, for example produced by optoelectronic devices, such as light emitting diodes (LEDs).

In one embodiment, a combination of first light having a wavelength of 405 nm±10 nm, second light having a wavelength of 810 nm±15 nm, third light having a wavelength of 780 nm±10 nm, and fourth light having a wavelength of 830 ±15 nm, is used, the first, the second the third and fourth lights comprising non-coherent light, for example produced by optoelectronic devices, such as light emitting diodes (LEDs).

In one embodiment, the light used for photodynamic therapy consists of a first light having high energy photons with a majority energy between 2.8 eV and 3.5 eV; and a second light having low energy photons with a majority energy between 1.24 eV and 1.65 eV, the first and the second light preferably being produced by optoelectronic devices, such as light emitting diodes (LEDs).

The term "with a majority energy" denotes in particular that at least 50%, in particular at least 60% or at least 70% or at least 80% or at least 90% or at least 95%, of the photons—as indicated by their energy—have the indicated energy.

Typically, the optoelectronic device is capable of emitting light, in particular non-coherent light, at a first wavelength from 400 to 430 nm, preferably at a dosage of 1 to 120 $J/cm^2$, and in particular with a power density of from about 10 to about 2500 $mW/cm^2$ for a period of time from 0.5 s to 120 min, and at a second wavelength from 780 to 830 nm, preferably at a dosage of 1 to 120 $J/cm^2$, and in particular with a power density of from about 10 to about 2500 $mW/cm^2$ for a period of time from 0.5 s to 120 min.

In particular, the optoelectronic device comprising light-emitting diode(s) (i.e. LEDs) as a light source.

In one embodiment, the photosensitizer is contacted with the infected area, i.e. with micro-organisms, such as bacteria, virus and fungus, in the target tissue, such as in biofilm, saliva, skin, plaque and on teeth surfaces or mucous membranes, by applying it, preferably directly, on the target. The photosensitizer can be applied in the form of an aqueous solution, an alcohol containing solution, a hydrophilic gel, a hydrophobic gel, a hydrophilic polymer, a hydrophobic polymer or a paste, lotion, tape, tablet, plaster or band-aid.

In one embodiment, the area target tissue subjected to photodynamic therapy is smaller than the total area of the skin, in particular the area is typically 10% or less of the total area, in particular 1% or less of the total area of the skin of the subject.

In one embodiment, the area of the target tissue subjected to photodynamic therapy is less than about 250 $cm^2$, for example less than about 100 $cm^2$, such as less than 50 $cm^2$, in particular less than 40 $cm^2$, for example 1 to 30 $cm^2$.

One embodiment comprises topically administering to the target tissue an antibiotic. Such an antibiotic may also function as a photosensitizer.

Based on the above, one embodiment comprises systemically administered antibiotic for use in antimicrobial photodynamic therapy of local microbial infections. Typically, the photodynamic therapy is carried out for treatment of oral diseases, such as periodontal diseases.

Thus, in one embodiment, the systemically administered antibiotic is used in photodynamic therapy carried out for treatment of bacterial biofilm, such as gumline bacterial biofilm.

Particularly preferred embodiments are represented by systemically administered antibiotic for use in antimicrobial photodynamic therapy, wherein the systemic antibiotic is selected from the group of photosensitive antibiotics of the group of azithromycin, tetracycline, macrolide, and combinations thereof.

Based on the above, in one preferred embodiment, the antibacterial effectivity of doxycycline is enhanced through light excitation of the doxycycline with using light having a wavelength in the range from 470 nm to 370 nm. In one embodiment, light of a wavelength of 405 nm is used.

In one embodiment, the systemically administered antibiotic for use in antimicrobial photodynamic therapy comprises a cyclic photoactive antibiotic for inhibiting collagenase 2 enzyme, matrix metalloproteinase 8, PMN Leukocyte collagenase, PMNL collagenase, neutrophil collagenase. Typically, the cyclic photoactive antibiotic is doxycycline or minocycline.

One embodiment relates to a method of enhancing the enzyme inhibition action of a pharmaceutical substance having an antimicrobial activity, comprising
    systemically administering a photosensitive pharmaceutical substance to a subject having a microbial infection in a target tissue to provide a plasma concentration of said substance in the subject;
    allowing the plasma concentration of the antibiotic increase to a predetermined level; and
    subjecting the target tissue to photodynamic therapy in order to increase the enzyme inhibition action of the substance in the target tissue.

One embodiment of this method comprises the use of cyclic photoactive antibiotics for inhibition of collagenase enzyme activity. Typically, the cyclic photoactive antibiotic, such as doxycycline or minocycline, is used for inhibiting MMP-8, MMP-9, MMP-13 or MMP-1 action or their gene expression or any of their combinations.

In one embodiment, a high concentration of a photoactive macrolide antibiotic, such as azithromycin, erythromycin, clarithromycin or roxithromycin is achieved within tissues, especially within the white blood cells with intraoral administration of the drug and the light activation is used to enhance drugs immunomodulatory actions and to reduce tissue inflammatory response.

In one embodiment, a photoactive macrolide antibiotic, such as azithromycin, erythromycin, clarithromycin or roxithromycin is used to provide a reduction of IL-6 and 8, MMP-1, 2, 9, 10 and 13, and GM-CSF gene expression.

One embodiment of this method comprises the use of cyclic photoactive antibiotics for inhibition of collagenase enzyme activity. Typically, the cyclic photoactive antibiotic, such as clarithromycine is used for inhibiting suppresses induction of monocyte chemoattractant protein-1 and MMP-action or their gene expression or any of their combinations In still a further embodiment, a method is provided for enhancing the enzyme inhibition action of a cyclic photoactive antibiotic for inhibition of collagenase enzyme activity. The method comprises the steps of
    systemically administering a photosensitive pharmaceutical substance to a subject having a microbial infection in a target tissue to provide a plasma concentration of said antibiotic in subject;
    allowing the plasma concentration of the antibiotic increase to a predetermined level; and
    subjecting the target tissue to photodynamic therapy in order to increase the antibiotic action of the antibiotic in the target tissue.

In any of the above embodiments, the light preferably comprises non-coherent light, for example produced by optoelectronic devices, such as light emitting diodes (LEDs).

The following embodiments are considered particularly preferred:
    In one embodiment, an azithromycin effect is enhanced in case of mosquito bite to decrease the possibility of malaria infection.

In one embodiment, tetracycline effect is enhanced to decrease the possibility of, or treat a rickettsia genus caused disease in case of arthropod bite, including chigger, ticks, fleas, and lice.

In one embodiment, systemic antibiotic administration is used to produce locally enhanceable antifungal effect in the treatment of onychomycosis.

In one embodiment, systemically administered tetracycline or macrolide antibiotic action is enhanced locally at the bite site of Inoxus tick to reduce the possibility of borreliosis infection.

In one embodiment, systemically administered antibiotic action is enhanced during treatment of pharyngitis with the application of light to pharynx area.

In one embodiment, the antimicrobial action of systemically administered antibiotic is enhanced by light in cases of otitis media infection, where antiviral action is needed as well as a widening of the antibacterial spectrum.

In one embodiment, a large dose of photosensitizing antibiotic is administered as a single dose or in sparsely manner in combination with the light enhancement to minimize the total dose of antibiotic use while keeping the treatment efficacy constant.

In one embodiment, the use of photosensitizing antibiotic in combination of light is used together with locally administered photosensitizing agent to further enhance the effect.

In one embodiment, azithromycin, or other systemically administered photosensitizing agent thereof, is used in the antimicrobial treatment.

Several antibiotic molecules, such as tetracyclines and macrolides act as photosensitizers, in addition to their basic antibiotic function. The photosensitizing action has been acknowledged as photosensitivity during antibiotic treatment. For example, the photosensitivity of doxycycline and azithromycin must be acknowledged during the treatment period, due to which the patients are advised to avoid direct sunlight. The photosensitivity is caused by the ability of the antibiotic molecule to absorb light of specific wavelength and emit the light forward to activate a nearby oxygen molecules, providing reactive oxygen species (ROS). Singlet oxygen is the most potent of the ROS species, due to the relatively long half-life of microseconds. However, these reactive oxygen species are toxic to several kind of microbes, including bacteria, viruses, fungi and parasites. This mechanism is known as antimicrobial photodynamic therapy (aPDT).

In the present technology, antibiotic molecules absorb for example low wavelength light. These wavelengths are usually well absorbed in skin tissue. Thus, the photosensitizing as herein described is generally well tolerated.

Based on the above, the present technology also provides a kit for achieving enhanced antimicrobial action of systemically administered antibiotic.

The kit comprises at least two components, viz. an optoelectronic component or device thereof and at least one systemically administered antibiotic. The optoelectronic component or device is capable of simultaneously emitting a first light consisting of high energy and a second light consisting of low energy photons. Typically, said first and said second light amount to at least 50% of all light emitted from the optoelectronic component or device.

The antibiotic is preferably selected from the group of macrolides, including but not restricted to levofloxacin, ofloxacin, ciprofloxacin, clarithromycin, erythromycin, roxithromycin, or azithromycin; tetracyclines including doxycycline, ionocycline, tetracycline, chlortetracycline, demeclocycline, lymecycline, meclocycline, methacycline, rolitetracycline, tigecycline, eravacycline, sarecycline, omacycline, sarecycline, eravacycline, omadacycline, oxytetracycline, colchicine, trimethoprim, metronidatzole. In particular the antibiotic is azithromycin, doxycycline, minocycline or colchicine or metronidatzole, or any of their combinations.

In one embodiment, the kit is used for inhibition of collagenase enzyme activity by using cyclic photoactive antibiotics.

In one embodiment, the kit contains a pharmaceutically acceptable composition of the antibiotic suitable for administration orally, parenterally or transdermally.

In one embodiment, the kit comprises further a photosensitizer. The photosensitizer is for example of a kind which can be activated by at least either of the high energy and low energy photons, preferably both. Examples include Hypericin, curcumin, phenalenone derivatives, Cercosporin, psoralen, xanthotoxin, Angelicin, alpha-Terthienyl, Phenylthepatriyne, THC, Cannabidiol (CBD). Synthetic photosensitizers include the following: RB (Rose Bengal), MB, Porphyrin derivatives, Curcumin derivatives, Methylene Blue, Indocyanine Green, Erythosine, Phenalenone derivatives, Fullerene derivatives, Xanthene derivates and combinations thereof.

In one embodiment, the photosensitizer is formulated for topical application. Preferably, the photosensitizer is in the form of a water soluble effervescent tablet, gel, or paste.

The following non-limiting examples illustrate embodiments of the present technology.

Antibiotic Susceptibility Test

Figure 1:
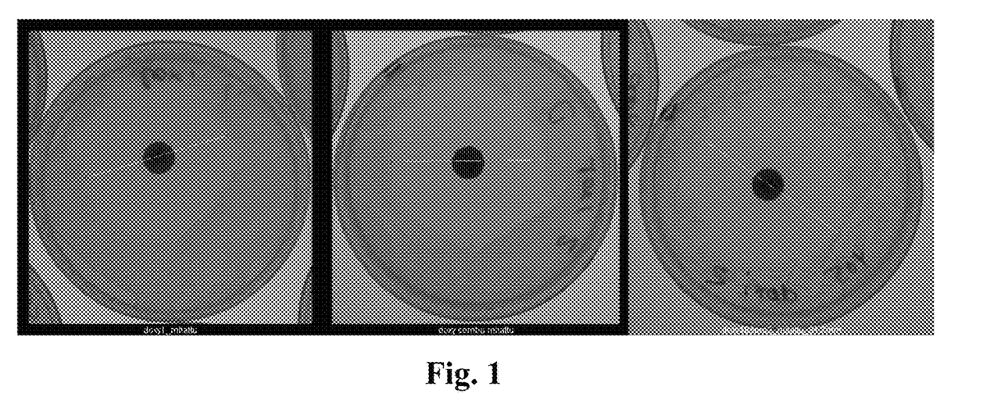
FIG. 1 shows three photographs indicating doxycycline effectivity tests carried out on petri dishes.

Each test was repeated 3 times with identical treatment and growth parameters. The calculated CFU:s for 100 J/cm$^2$ treated doxycycline disc results are shown in table 1 and representing image of difference between treated and nontreated doxy petri dish are shown in FIG. 1.

TABLE 1

Antibiotic effectivity test

| Column1 | doxycycline (no light) | doxycycline (44 J/cm$^2$, 405 nm + 60 J/cm$^2$ 810 nm) | doxycycline (83 J/cm$^2$, 405 nm) | control |
| --- | --- | --- | --- | --- |
| Regression diameter | 26,33333 | 29,66666667 | 30,33333 | 0 |

FIG. 1 shows the effectivity of doxycycline. Starting from the left is the doxycycline inhibition effect in dark, in the middle the resulting petri dish with 405 nm and 810 nm exposure and on the right side the petri dish with 405 nm excitation is shown.

As will appear, a clear increase in the effectivity of the can be seen for dishes that had been subjected to light.

Figure 2:
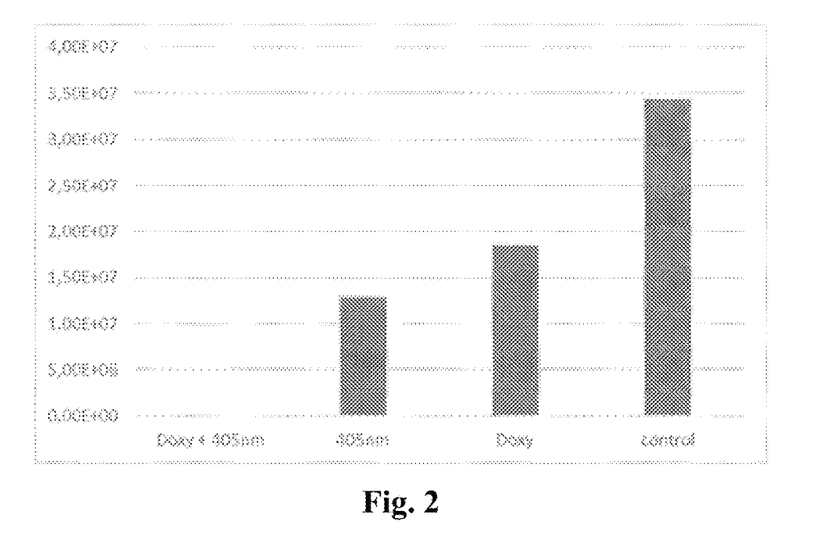
FIG. 2 is a bar chart showing bacteria growth of *Streptococcus mutans* for four different treatments, illustrating the effect of light activation of doxycycline against planktonic *Streptococcus mutans*.

FIG. 2 is a bar chart showing light activation of doxycycline at 405 nm in a planktonic bacteria test. As will appear, doxycycline was bacteria static but failed to reduce bacteria growth below 10$^7$ CFU. By contrast, light activated doxycycline was highly effective and resulted in bactericidal effect of over 3 log bacteria killing. 100 J of antibacterial blue light had minor reduction in CFU compared to non-exposed control.

Figure 3:
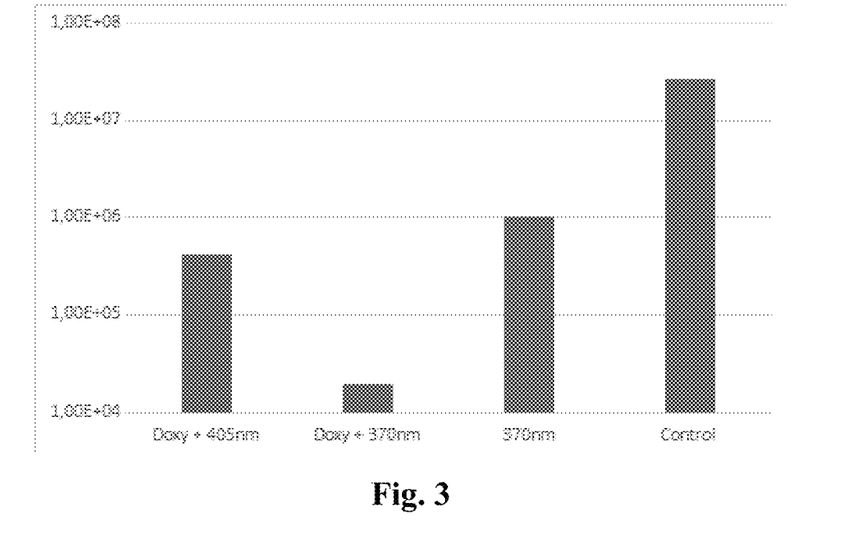
FIG. 3 is a bar chart showing a comparison of the doxycycline effect with light excitations of 405 nm, dual-light (810 nm & 405 nm) and 370 nm to *Streptococcus mutans* colony formation in 4 day biofilm model.

FIG. 3 is a bar chart showing a comparison of doxycycline effect with light excitations of 405 nm and 370 nm on *Streptococcus mutans* colony formation in a 4-day biofilm effectivity test.

As will appear, light excited doxycycline was substantially more effective than dark control, and both antibacterial light effects were improved by over 1.5 log with the addition of doxycycline.

Figure 4:
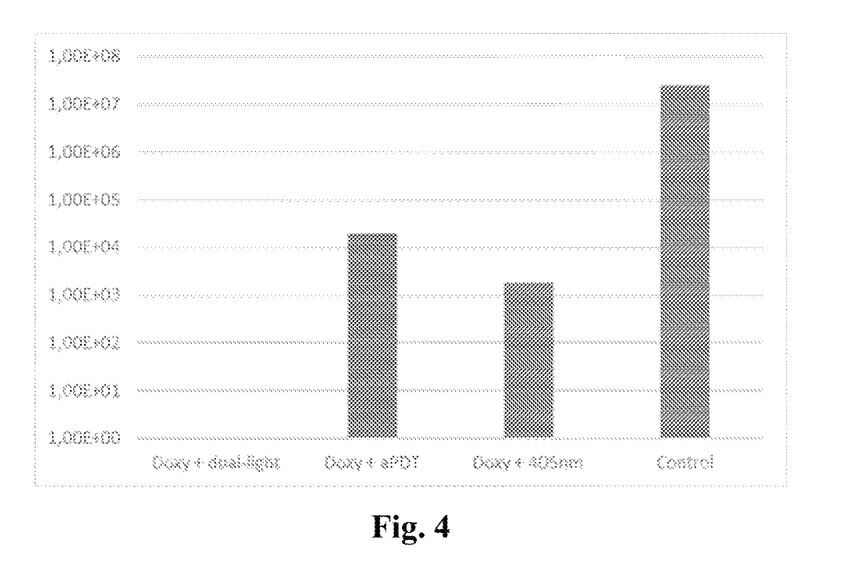
FIG. 4 is a bar chart showing the doxycycline effect against *Streptococcus mutans* 4 day biofilm for light excitation using a combination of light of 405 nm and 810 nm ("dual-light") together with an ICG sensitizer, compared with light of 810 nm together with an ICG sensitizer ("doxy+aPDT") and with 405 nm light without ICG sensitizer ("405"). A control of doxycycline is given as a reference.
Figure 5:
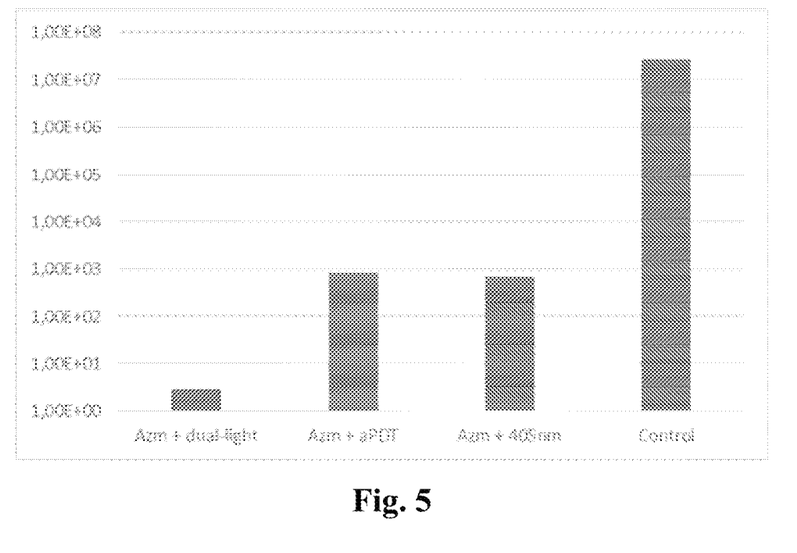
FIG. 5 is a bar chart showing the azithromycin effect against *Streptococcus mutans* 4 day biofilm for light excitation using a combination light of 405 nm and 810 nm ("dual-light") together with an ICG sensitizer, compared with light of 810 nm together with an ICG sensitizer ("Azm+aPDT") and with 405 nm light without ICG sensitizer ("405"). A control of azithromycin is given as a reference.

FIG. 4 gives the CFU:s for *Streptococcus mutans* colonies on petri dishes after 4-day treatments, repeated 6 times with identical treatment and growth parameters, for four series of tests. The first (non-existent) bar represents the CFU:s for *S. mutans* colonies doxycycline which had been treated with doxycycline (30 μg) and dual light of 405 nm and 810 nm together with Indocyanine Green. The energy intensity of the light was 100 J/cm$^2$. The second bar represents the CFU:s for *S. mutans* colonies which had been treated with doxycycline and light of 405 nm (having an energy intensity of 100 J/cm$^2$) together with Indocyanine Green. The third bar represents the CFU:s for *S. mutans* colonies which had been treated with doxycycline and light of 405 nm (100 J/cm$^2$).

As can be seen, for light treatments, the results are better than for the control (doxycycline as such), and particularly good results are obtained for the dual light (405 nm and 810 nm together with Indocyanine Green). Further, although good results were obtained from dual light wherein the energy intensity ratio between the high energy and low energy light was generally in the range of 3:1 to 1:3, the best results were obtained for ratios of about 1.05:1 to 1:1.05.

A further series of tests was carried out for *Streptococcus mutans* biofilms using Azithromycine (15 μg) and Indocyanine Green using light at 100 J/cm$^2$. For 1 day biofilms, the CFU was on an average <1 after treatment with dual light of 405 nm and 810 nm, respectively (at ratios of 3:1 to 1:3), whereas for either 405 nm or 810 nm wavelength light alone, the CFU was on an average below 100 after 1 day. For Azithromycine and Indocyanine Green without light, the CFU was about 1E06 to 1E07 after 1 day.

The invention claimed is:

1. A method of enhancing the antimicrobial action of a photosensitive antibiotic, comprising:
   systemically administering the photosensitive antibiotic to a subject having a microbial infection in a target tissue to provide a tissue concentration of the photosensitive antibiotic in the subject, wherein the photosensitive antibiotic comprises a tetracycline or a macrolide compound, and wherein the microbial infection is at least partially susceptible to treatment with the tetracycline or macrolide compound; and
   subjecting the target tissue to photodynamic therapy in order to enhance the antimicrobial action of the photosensitive antibiotic in the target tissue relative to the antimicrobial action of the photosensitive antibiotic without the photodynamic therapy, wherein the photodynamic therapy comprises subjecting the target tissue to a first light having a first light energy and to a second light having a second light energy simultaneously directed against the target tissue, and wherein the energy intensity ratio between the first light energy and the second light energy is in the range of 3:1 to 1:3.

2. The method according to claim 1, wherein the microbial infection is caused by virus, bacteria or fungus.

3. The method according to claim 1, wherein the microbial infection to be treated is caused by gram-positive bacteria selected from bacteria of the streptococci or staphylococci species or gram-negative bacteria selected from the group consisting of *Proteobacteria, Aquificae, Chlamydiae, Bacteroidetes, Chlorobi, Cyanobacteria, Fibrobacteres, Verrucomicrobia, Planctomycetes, Spirochetes, Acidobacteria, Actinobacteria, Firmicutes, Thermotogae, Porphyromonas* and *Chloroflexi*.

4. The method according to claim 1, wherein the antibiotic action is enhanced to antiviral action and the microbial infection to be treated is caused by a virus selected from the group consisting of Adenoviruses, Herpesviruses, Poxviruses, Parvoviruses, Reoviruses, Picornaviruses, Togaviruses, Orthomyxoviruses, Rhabdoviruses, Retroviruses, Papillomavirus, and Hepadnaviruses.

5. The method according to claim 1, wherein the photosensitive antibiotic is selected from the group consisting of azithromycin, doxycycline, minocycline, and combinations thereof.

6. The method according to claim 1, comprising administering the photosensitive antibiotic orally or parenterally.

7. The method according to claim 1, comprising raising the tissue concentration of the photosensitive antibiotic by oral mucosal delivery.

8. The method according to claim 1, comprising raising the antibiotic concentration in a Gingival Precrevicular Fluid.

9. The method according to claim 1, comprising allowing the tissue concentration of the antibiotic increase to a predetermined level of the administered antibiotics' maximum tissue concentration before subjecting the target tissue to the photodynamic therapy.

10. The method according to claim 1, wherein the target tissue comprises soft tissues, biofilms, saliva, skin, plaque and teeth surfaces, and mucous membranes.

11. The method according to claim 1, wherein the target tissue comprises oral tissue.

12. The method according to claim 1, wherein the microbial infection of the target tissue comprises a gumline bacterial biofilm.

13. The method according to claim 1, wherein the target tissue comprises tissue in the throat, in the nose, or in the ears.

14. The method according to claim 13, wherein the microbial infection of the target tissue comprises pharyngitis or otitis.

15. The method according to claim 1, wherein the target tissue is topically subjected to the photodynamic therapy.

16. The method according to claim 1, wherein the antibiotic is photoactivated in order to eliminate pathogens inside tissue and host cells.

17. The method according to claim 1, wherein the photodynamic therapy comprises subjecting the target tissue to electromagnetic radiation in the form of light of either or two of the following energy levels: a first light with photons having a majority energy in the range from 3.5 eV to 2.8 eV, and a second light with photons having a majority energy in the range from 1.24 eV to 2.48 eV.

18. The method according to claim 17, wherein:
   non-coherent radiant light energy is generated at one first energy level;
   from the non-coherent radiant light energy there is provided a first light having a wavelength corresponding to the majority energy of the first energy level, and optionally a second light having a wavelength corresponding to the majority energy of the second energy level; and
   the first and the second light are simultaneously directed against the target tissue.

19. The method according to claim 1, wherein the first light has a wavelength in the range of about 350 to 450 nm, and the second light has a wavelength in the range of about 500 to 1000 nm.

20. The method according to claim 19, wherein the photodynamic therapy comprises subjecting the target tissue to a first light having a wavelength of 405 nm±10 nm and a second light having a wavelength of 810 nm±15 nm, both the first and the second lights comprising non-coherent light produced by optoelectronic devices.

21. The method according to claim 1, wherein the target tissue is subjected to endogenous and exogenous excitement so as to generate reactive oxygen singlets or reactive oxygen species, or both.

22. The method according to claim 1, wherein light is combined with at least one photosensitive substance for treating the target tissue using the photodynamic therapy.

23. The method according to claim 22, wherein the photosensitive substance is selected from the group consisting of Hypericin, curcumin, phenalenone derivatives, Cercosporin, psoralen, xanthotoxin, Angelicin, alpha-Terthienyl, Phenylthepatriyne, THC, Cannabidiol (CBD), RB (Rose Bengal), MB, Porphyrin derivatives, Curcumin derivatives, Methylene Blue, Indocyanine Green, Erythosine, Phenalenone derivatives, Fullerene derivatives, Xanthene derivates, and combinations thereof.

24. The method according to claim 17, wherein the photons of the first light and/or the second light are applied in conjugation with at least one exogeneous photosensitizer.

25. The method according to claim 1, wherein a photosensitizer is provided for topical treatment of mammalian tissue, wherein said photosensitizer is applied to a superficial part of the tissue, and wherein the part thus treated is subsequently or simultaneously subjected to light at two different wavelengths.

26. The method according to claim 1, wherein a photosensitizer is contacted with micro-organisms in the target tissue by applying it on the target in the form of an aqueous solution, an alcohol-containing solution, a hydrophilic gel, a hydrophobic gel, a hydrophilic polymer, a hydrophobic polymer or a paste, lotion, tape, tablet, plaster or band-aid.

27. The method according to claim 1, wherein the area of the target tissue subjected to photodynamic therapy is less than 50 cm$^2$.

28. The method according to claim 1, comprising topically administering the photosensitive antibiotic to the target tissue.

29. A method for treating a periodontal disease in a subject, comprising:
systemically administering a photosensitive pharmaceutical substance to the subject to provide a tissue concentration of said photosensitive pharmaceutical substance in the subject;
optionally allowing the tissue concentration of the photosensitive pharmaceutical substance to increase to a predetermined level; and
subjecting the target tissue to photodynamic therapy in order to increase the collagenase enzyme inhibition action of the photosensitive pharmaceutical substance in the target tissue relative to the collagenase enzyme inhibition action of the cyclic photoactive antibiotic without the photodynamic therapy,
wherein the photodynamic therapy comprises subjecting the target tissue to a first light having a first light energy and to a second light having a second light energy simultaneously directed against the target tissue,
wherein the energy intensity ratio between the first light energy and the second light energy is in the range of 3:1 to 1:3, and
wherein the photosensitive pharmaceutical substance comprises doxycycline or minocycline.

30. The method according to claim 29, wherein the doxycycline or minocycline inhibits MMP-8, MMP-9, MMP-13 or MMP-1 action, their gene expression, or any combination thereof.

31. A method of enhancing the enzyme inhibition action of a cyclic photoactive antibiotic for inhibition of collagenase enzyme activity, comprising:
systemically administering the cyclic photoactive antibiotic to a subject having a microbial infection in a target tissue to provide a tissue concentration of said cyclic photoactive antibiotic in said subject;
optionally allowing the tissue concentration of the cyclic photoactive antibiotic to increase to a predetermined level; and
subjecting the target tissue to photodynamic therapy in order to increase the collagenase enzyme inhibition action of the cyclic photoactive antibiotic in the target tissue relative to the collagenase enzyme inhibition action of the cyclic photoactive antibiotic without the photodynamic therapy,
wherein the photodynamic therapy comprises subjecting the target tissue to a first light having a first light energy and to a second light having a second light energy simultaneously directed against the target tissue, and
wherein the energy intensity ratio between the first light energy and the second light energy is in the range of 3:1 to 1:3.

32. The method according to claim 1, wherein the target tissue comprises gum tissue, skin, or mucosa.

33. The method according to claim 1, wherein the energy intensity ratio between the first light energy and the second light energy is in the range of 1.05:1 to 1:1.05.

* * * * *